United States Patent
Atkinson et al.

[11] Patent Number: 6,067,167
[45] Date of Patent: May 23, 2000

[54] ILS SENSORS FOR DRUG DETECTION WITHIN VEHICLES

[75] Inventors: George H. Atkinson; Markus A. Wolperdinger, both of Tucson, Ariz.

[73] Assignee: Innovative Lasers Corp., Tucson, Ariz.

[21] Appl. No.: 09/317,663

[22] Filed: May 24, 1999

Related U.S. Application Data

[63] Continuation-in-part of application No. 09/131,437, Aug. 10, 1998, Pat. No. 5,907,407.

[51] Int. Cl.$^7$ .................................................. G01N 21/00
[52] U.S. Cl. ........................... 356/437; 326/442; 326/439
[58] Field of Search .................................... 356/437, 436, 356/326, 442, 439

[56] References Cited

U.S. PATENT DOCUMENTS

| | | | |
|---|---|---|---|
| 5,349,187 | 9/1994 | Azzazy et al. | 250/338.5 |
| 5,689,334 | 11/1997 | Atkinson et al. | 356/326 |
| 5,723,864 | 3/1998 | Atkinson et al. | 250/339.13 |
| 5,742,054 | 4/1998 | Atkinson | 250/339.13 |
| 5,747,807 | 5/1998 | Atkinson et al. | 250/339.13 |
| 5,907,407 | 5/1999 | Atkinson et al. | 356/437 |

OTHER PUBLICATIONS

A.W. Jones, "Precision, Accuracy and Relevance of Breath Alcohol Measurements", Modern Problems of Pharmacopsychiatry, vol. 11, pp. 65–78 (1976).
A.R. Gennaro, Spectra work book, Sadtler Research Laboratories, Inc. (1966–1968).
H.L. Fang et al, "Molecular Conformers In Gas–Phase Ethanol: A Temperature Study Of Vibrational Overtones", Chemical Physics Letters, vol. 105, pp. 5–11 (1984).
L.S. Rothman, "The Hitran Molecular Database", J. Quant. Spectrosc. Radiat. Transf., vol. 48, pp. 5/6 (1992).

*Primary Examiner*—Frank G. Font
*Assistant Examiner*—Reginald A. Ratliff
*Attorney, Agent, or Firm*—Benmen & Collins

[57] ABSTRACT

On-board ILS sensors for detecting illegal drugs and based on intracavity laser spectroscopy (ILS) are provided for detecting the presence of drugs and their metabolized by-product vapors in an enclosed space, such as a vehicle. The sensor comprises: (a) a laser comprising a gain medium having two opposed facets within a laser resonator and functioning as an intracavity spectroscopic device having a first end and a second end, the first end operatively associated with a partially reflecting (i.e., partially transmitting) surface; (b) a reflective or dispersive optical element (e.g., a mirror or a diffraction grating) operatively associated with the second end to define a broadband wavelength laser resonator between the optical element and the first end and to thereby define an external cavity region between at least one facet of the gain medium and either the first end or the second end or both ends; (c) the external cavity region being exposed to air in the enclosed space to enable any drugs or their metabolized by-product molecules to enter thereinto; (d) a detector spaced from the first end; (e) appropriate electronics for measuring and analyzing the detector signal; (f) a housing for containing at least the laser, the partially reflecting surface, and the optical element, the housing being configured to prevent escape of stray radiation into the enclosed space and to permit air from the enclosed space to continuously circulate through the external cavity region for analysis; and (g) means for driving the laser (e.g., electrical or optical). A method is provided for measuring concentration of drug vapors and their metabolized by-product vapors in the vehicle or other enclosed space employing the on-board sensor. The method comprises: (1) sensing any drugs and their metabolized by-product vapors in the enclosed space by the on-board sensor; and (2) providing a signal indicative of presence of any drugs or metabolized vapors.

22 Claims, 4 Drawing Sheets

ILS SENSORS FOR DRUG DETECTION WITHIN VEHICLES

CROSS-REFERENCE TO RELATED APPLICATION

The present application is a continuation-in-part of application Ser. No. 09/131,437, filed Aug. 10, 1998 now U.S. Pat. No. 5,907,407.

TECHNICAL FIELD

The present invention relates generally to sensors for detecting drug vapors, or vapors resulting from metabolized by-products of drugs in the human body, and, more particularly, to on-board sensors employing intracavity laser spectroscopy (ILS) to detect the presence of one or more drugs in intoxicated drivers in vehicles and in other enclosed spaces, such as cargo areas.

BACKGROUND ART

Detecting drug-impaired drivers has gained a high level of importance during the last decade. In most cases, the reason to identify drug-impaired individuals participating in public traffic is motivated by safety issues and legal implications caused by these individuals operating cars, machinery or other equipment. Safety and legal issues are both very important in the context of a mobile society heavily relying on motorized vehicles for transportation. Financial implications for individuals or groups of the society resulting from accidents are considerable. Recognizing the importance of these facts, the abatement of drug-related accidents has been identified as prime target by the U.S. government.

Conventional technology utilized for drug detection in general relies on a variety of different analytical methods, e.g., GC, HPLC, MS, GC-MS, etc. Most commonly, chemical or physico-chemical methods are employed to analyze the drug composition and the drug contents of urine or blood samples. However, these approaches are time-consuming, require expensive equipment and well trained operators, and may necessitate medical supervision.

The detection of drug vapors or vapors resulting from metabolization of drugs in the human body in traffic and traffic-related situations, although of great importance, is a much less explored field. Almost all known methodologies are limited to laboratory applications, due to the fact that test procedures are time consuming and complicated; stationary equipment is required to conduct the tests. Only recently, a sampling method for cocaine vapor in cargo containers has been used by the Canadian Customs; see, Detection of Drugs in Cargo Containers by High Volume Air Sampling, P. Neudorfl, et al., SPIE Conference, Boston, Mass. (November 1996).

Most conventional analytical methods used for drug detection are based on technologies which can only be applied external to a vehicle and require the cooperation of tested individuals, with authorities conducting the drug test. None of them is suitable for providing real-time information about the presence of drugs in the field. In addition to this, most conventional methods share several significant shortcomings:

(a) Only selected vehicles or individuals can be tested for drugs, due to logistical and personnel limitations, leading to a high percent rate of undetected drugs.

(b) Vehicles with drivers suspected of being under the influence of drugs have to be stopped, necessitating costly checkpoints and follow-up examinations.

(c) Expensive equipment has to be set up and maintained at high cost.

(d) Human interaction is required, accounting for a variety of different problems, e.g., high personnel costs, risk of violent encounters, etc.

(e) Testing is sporadic and does not provide continuous monitoring of traffic and vehicles.

These facts lead to the conclusion, that (i) conventional technologies available to identify drugs in traffic-related situations are limited in their applicability and (ii) due to their conceptual shortcomings, these methods are even less suited to contribute to a significant further reduction of drug related situations in traffic as required by the government.

The above-identified patent application Ser. No. 09/131, 437 discloses and claims small, highly-sensitive, on-board alcohol detectors. The on-board alcohol detector is mounted within the cabin area of vehicles. However, the prior art for detectors useful for detecting drugs, or the metabolized by-products of drug ingestion, is even less well-developed than the prior art for alcohol detectors. Accordingly, there is a need for a new generation of small, highly-sensitive, on-board detectors which would help to greatly reduce the number of drug-impaired drivers by preventing individuals under the influence from driving vehicles. These sensors, mounted within the cabin area of vehicles, would address the problem of driving under the influence before it even arises. These small and highly sensitive drug detectors could also be used to detect drugs or by-products of drugs in other enclosed spaces.

DISCLOSURE OF INVENTION

In accordance with the present invention, sensors for detecting drugs or the metabolized by-products of drugs based on intracavity laser spectroscopy (ILS) meet these requirements and provide the potential to extend drug detection beyond the performance available from the current, state-of-the-art detection technologies. An on-board ILS sensor for detecting the presence of drug-based vapors due to the presence of drugs and/or emitted by a driver in a cabin of a vehicle is provided that comprises:

(a) a laser comprising a gain medium having two opposed facets within a laser resonator and functioning as an intracavity spectroscopic device having a first end and a second end, the first end operatively associated with a partially reflecting (i.e., partially transmitting) surface;

(b) a reflective or dispersive optical element (e.g., a mirror or a diffraction grating) operatively associated with the second end to define a broadband wave-length laser resonator between the optical element and the first end and to thereby define an external cavity region between at least one facet of the gain medium and either the first end or the second end or both ends;

(c) the external cavity region being exposed to a sample of air representative of the air in the cabin of the vehicle to enable any molecules associated with drugs or metabolized by-products of drugs to enter thereinto;

(d) a detector spaced from the first end and providing an output detector signal;

(e) appropriate electronics for measuring and analyzing the detector signal;

(f) a housing for containing at least the laser, the partially reflecting surface, and the optical element, the housing being configured to prevent escape of stray radiation into the cabin and to permit air from the cabin to continuously circulate through the external cavity region for analysis; and (g) means for driving the laser (e.g., electrical or optical).

A focusing, expanding, or collimating intracavity optical element (e.g., a lens) to shape the beam may be placed in the external intracavity region.

A method is provided for measuring concentration of such drug-related vapors in a vehicle employing the above-described on-board sensor. The method comprises:

(1) sensing any drug-related vapors in the vehicle by the on-board sensor; and (2) providing a signal indicative of presence of any drug-related vapors.

The drugs of present interest, for which the apparatus and method of the present invention may be used, include marijuana, cocaine, heroin, and other drugs listed in the Controlled Substances Act (CSA) Database provided by the Drug Enforcement Administration (DEA), see, webpage of Drug Enforcement Agency at http://dea.gim.net. Further, the metabolized by-products of alcohol, including acetaldehyde and acetic acid, may also be detected in accordance with the teachings herein.

Other objects, features, and advantages of the present invention will become apparent upon consideration of the following detailed description and accompanying drawings, in which like reference designations represent like features throughout the FIGURES.

BRIEF DESCRIPTION OF THE DRAWINGS

The drawings referred to in this description should be understood as not being drawn to scale except if specifically noted.

BEST MODES FOR CARRYING OUT THE INVENTION

Reference is now made in detail to a specific embodiment of the present invention, which illustrates the best mode presently contemplated by the inventors for practicing the invention. Alternative embodiments are also briefly described as applicable.

In accordance with the present invention, an alternative concept to prior art approaches for on-board drug detection in traffic capitalizes on three important characteristics of the ILS technology: (i) high sensitivity; (ii) the ability to work with small volume gas samples, and (iii) continuous operation. This new concept derives from the installation of a small and inexpensive ILS drug sensor inside the vehicle that monitors the drug-vapor or metabolized drug-vapor content of the air continuously through a small input port situated in front of the driver.

The drugs of present interest, for which the apparatus and method of the present invention may be used, include marijuana, cocaine, heroin, and other drugs listed by the Controlled Substances Act (CSA) provided by the Drug Enforcement Administration (DEA). Further, detection may be made in the case of smoking a drug by detection of a specific known component in the drug smoke or in the case of ingestion of a drug, such as by eating, inhaling, or injecting a drug into the body by detection of a specific known metabolized by-product. In the former case, smoking marijuana may be detected by D9-Tetrahydrocannabinol (THC). In the latter case, known metabolized by-products include D9-tetrahydrocannabinol (THC) (for marijuana), ecgonine methyl ester (for cocaine), morphine-3-glucuronide (for heroin) etc. However, most of these metabolites are excreted in the urine and not in the breath of the user. There is very little information about exhaled metabolites. On the other hand, exhaled metabolites are known for other drugs, such as alcohol, in which the exhaled metabolites include acetaldehyde and acetic acid. To the extent that exhaled metabolites can be identified for the CSA-listed drugs, detection of use of such drugs may be performed in accordance with the teachings of the present invention.

ILS drug sensors employed as on-board sensors respond within seconds to changes in drug levels, thereby permitting permanent drug detection in both standing and moving vehicles without interrupting the flow of traffic. An on-board drug sensor would also respond to a situation where a drug is transported or smoked in the vehicle.

Once a drug has been detected inside the vehicle, there are a wide variety of options concerning how this information can be used. Drivers under the influence would not be able to start the vehicle (i.e., the ignition of the vehicle could be inhibited in the presence of the drug above a set threshold value) or a signal could be sent out by the sensor to a remote detection unit outside of the vehicle. If desirable, feedback from the sensor could be available for vehicle occupants, allowing them to make a responsible decision whether to use the vehicle or abstain from driving.

One important aspect of the on-board ILS drug sensor concept is the fact that it could eliminate the need for conventional drug testing in traffic-related situations, e.g., sobriety checkpoints. A readout of a car traveling normally on the road could be interrogated via a handheld "drug gun", or automatically at remote unmanned interrogation sites located at key locations. The identification of a drug-impaired driver could be radioed to a central location or the nearest patrol cars for action or using satellite communication for automated investigation of on-board sensors.

Not to be minimized with this new concept is the fact that the cooperation of the driver is not required in order to obtain a measurement of the drug concentrations. The vehicle does not have to slow down or drive through a special test fixture. All the driver must do is breathe normally.

The wavelength-laser energy combination utilized for the sensor operates within the so-called "eye safe region" so as to present no potential danger to eyes and skin of people occupying the vehicle. Since the on-board ILS drug sensor is completely enclosing the laser beam and the radiation is contained within the sensor housing, its use totally obviates any laser radiation damage concerns.

In summary, ILS-based sensors for drug detection in vehicles are anticipated to significantly facilitate and improve drug vapor detection by obviating many of the difficulties encountered in conventional approaches. On-board ILS drug sensors have a great potential to significantly reduce drug related incidents in traffic and, therefore, eliminating the need for many "after the fact" methodologies currently used to establish drug concentrations if an accident has occurred.

The following list summarizes the most important advantages of on-board ILS drug sensors:

- high sensitivity for vapors associated with drug metabolites
- fast response of sensor (in seconds);
- only small sample volumes required;
- continuous, real time monitoring of drug-related vapors while vehicle is moving (no need to stop the vehicle to determine the presence of a drug);
- light weight, small and rugged sensor design;
- all radiation contained physically, therefore, safe to human eyes and tissue;
- low cost of ownership, low maintenance costs, due to simple design;
- compatible with virtually every vehicle type;
- feedback of sensor reading to driver possible, if desired;
- remote, unmanned sensing of virtually every vehicle passing monitoring locations possible;
- no driver cooperation or interaction between driver and law enforcement officials required;
- drug detection in vehicles with windows either closed or opened (different sensitivity ranges may be utilized to address different degrees of dilution caused by open windows);
- no need for drug checkpoints; and
- cost reduction by investigation of suspect vehicles only.

The concept of optical ILS drug sensors, deployed inside vehicles and used as continuously operating on-board devices is described below. Important issues related to the functionality of the sensor as well as operational questions associated with sensor operation in vehicles are discussed in detail.

Optical on-board drug sensors, utilizing intracavity laser spectroscopy (ILS), can be envisioned as small, highly integrated devices. They are based on the principle of absorption enhancement inside a laser resonator taking advantage of high absorption gain achieved within small sample volumes. This approach has been successfully demonstrated by the inventors for different ILS laser configurations and for a wide variety of molecules; see, e.g., U.S. Pat. Nos. 5,689,334, issued Nov. 18, 1997; 5,723,864, issued Mar. 3, 1998; 5,742,054, issued Apr. 21, 1998; and 5,747,807, issued May 5, 1998, all to George H. Atkinson et al.

To develop and utilize ILS technology for small on-board drug sensors, a series of interrelated technical questions has to be addressed and resolved. These technical questions are:

What is the amount of airborne drug vapors and metabolized by-products generated by a drug-impaired driver in a vehicle under different conditions?

In which region of the optical spectrum can such drug vapors and metabolized by-products be detected in the vapor phase?

What is the minimum sensitivity an on-board drug sensor must achieve to allow for reliable drug detection?

What is the ILS laser design most suitable for small on-board drug sensors?

Are there any possible interferences with other airborne species present in the cabin?

What are possible safety hazards caused by the operation of on-board drug sensors in close proximity to vehicle occupants?

A key question concerning specifications for on-board drug sensors revolves around the concentration of drug vapors and metabolized by-product molecules in a vehicle cabin generated by a driver under the influence. Cocaine is one example for drugs consumed inside vehicles. The concentration of cocaine and its metabolized or decomposed by-products, such as ecgonine methyl ester, in a vehicle depends on many factors, e.g., number of occupants under the influence, their blood cocaine concentration, length of time that the occupants are inside the vehicle and the air exchange rate in the vehicle. The following calculations are based on single occupancy in a well ventilated vehicle and a cocaine consumption of 50 mg. Based on these factors, the cocaine concentration in the blood calculates to approximately 10 mg per liter blood, assuming a total amount of 5 liters of blood.

An aliquot part of the blood drug concentration is present in the breath of an individual after the consumption of the drug. The exact conversion factor is not known for cocaine, but it was suggested to range between 1000 and 100; see, "The Response of the Intoxilyzer 4011AS-A to a Number of Possible Interfacing Substances", J. M. Cowan, et al., *Journal of Forensic Sciences*, p. 797, (1990). For the purpose of converting between breath alcohol content and blood alcohol content in case of alcohol impaired drivers, a factor of 2100 is widely accepted; see, A. W. Jones, "Precision, Accuracy and Relevance of Breath Alcohol Measurements", *Modern Problems of Pharmacopsychiatry*, Vol. 11, pp. 65–78, 1976. Utilizing a conversion factor of 1000 in the case of cocaine, the concentration of cocaine in breath can be calculated to $10^{-5}$ g per liter breath which can be translated into $7.4 \times 10^{-7}$ cm$^3$ per 1 cm$^3$ breath.

Assuming a breathing rate of 15 times per minute with an average breath volume of 500 cm$^3$, then the volume of cocaine vapor generated per minute inside a closed vehicle cabin, based on single occupancy, can be calculated to be:

$$7.4 \times 10^{-7} \text{ cm}^3 \cdot 500 \cdot 15 = 5.5 \times 10^{-3} \text{ cm}^3/\text{minute}.$$

Assuming further the volume of a vehicle to be 2.5 m$^3$, then the concentration of cocaine vapor in a car with windows closed increases steadily and reaches a concentration in the parts per billion (ppb) range within minutes. The following table shows the cocaine vapor generation as a function of time under the described conditions. The calculation is based on a temperature of 20° C., a pressure of 760 Torr, and single occupancy in the vehicle.

TABLE I

Cocaine Vapor Concentration in a Vehicle as a Function of Time.

| Time [min] | Cocaine vapor concentration [ppb] |
|---|---|
| 0 | 0 |
| 5 | 11 |
| 10 | 22 |
| 30 | 66 |
| 60 | 132 |

Although sub-ppb drug concentrations in the vehicle cabin have to be assumed in the case of high air exchange rates (i.e., windows open, fan on), the drug concentration in the vicinity of the driver is much higher and can be estimated to reach ppb levels, if not higher. Considering the fact that small on-board sensors can be placed in close proximity to the location of the highest drug concentration (i.e., next to the driver's head), high air exchange rates are not expected to present a particular challenge for on-board ILS drug sensors.

Choosing the appropriate spectral region for drug detection is critical to achieve high sensitivity and to avoid interference with other airborne species present in a vehicle. At the same time, operational limitations of ILS laser and signal detector have to be considered and lead to a restriction of the usable wavelength regions.

Taking these considerations into account, a wavelength range from 1 to 4 $\mu$m was selected for a detailed analysis.

Figure 1:
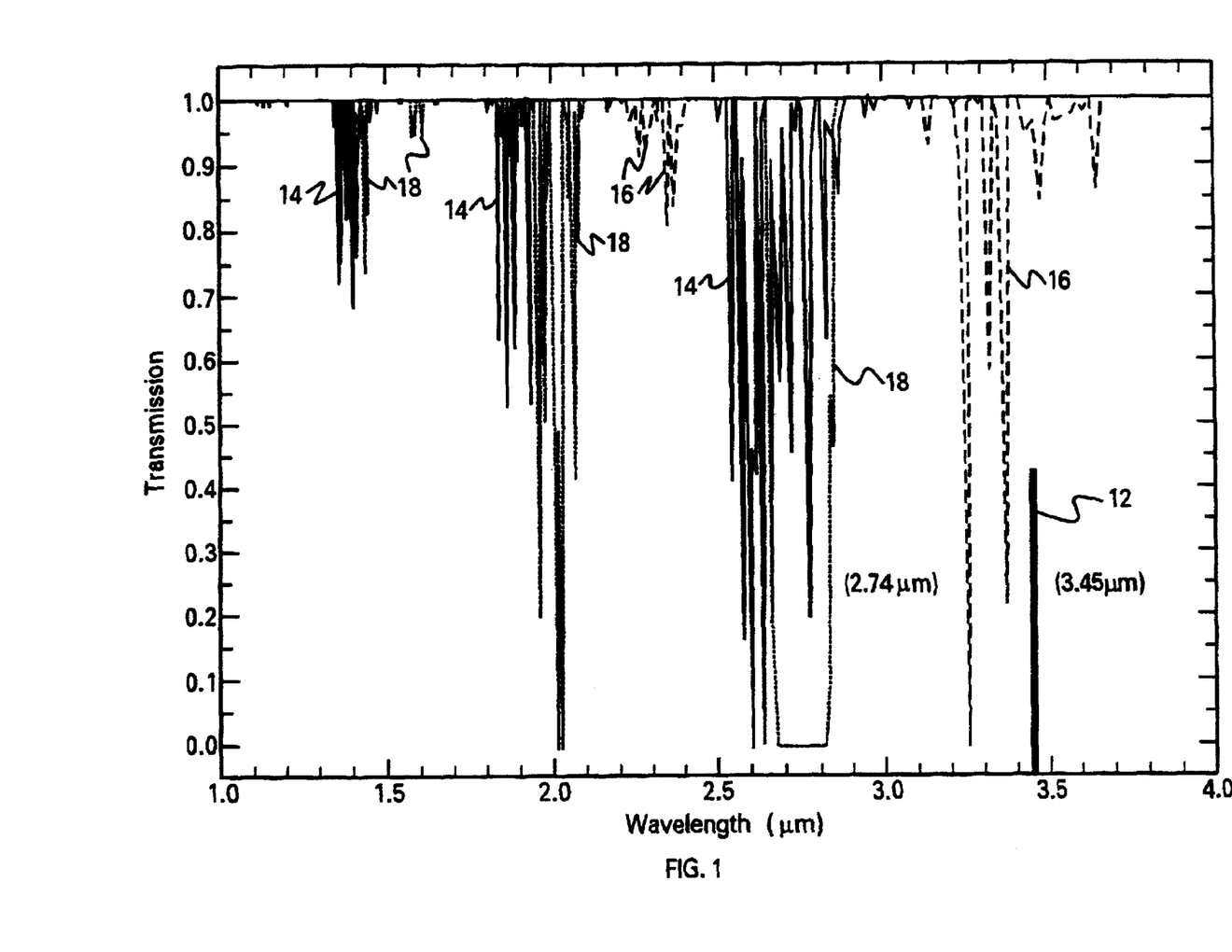
FIG. 1, on coordinates of transmission and wavelength (in $\mu$m), is a plot of cocaine vapor absorption between 1 and 4 $\mu$m, showing also absorption of water ($H_2O$), methane ($CH_4$), and carbon dioxide ($CO_2$) in the same range, which are examples of other gaseous species found in air that might be considered as spectral interferents.

Although the absorption spectrum of cocaine is unavailable, it can be concluded from structurally similar substances that the cocaine spectrum will have absorption peaks around 3.4 $\mu$m. FIG. 1 summarizes the expected prominent absorption region of cocaine between 1 $\mu$m and 4 $\mu$m, as well as absorption features of other molecules absorbing in this wavelength region. The cocaine absorption wavelength is denoted as 12 (3.45 $\mu$m). The absorption of water is indicated by Curve 14, the absorption of methane by Curve 16, and the absorption of carbon dioxide by Curve 18.

The ability to detect molecules with very small absorption cross sections is a unique feature of ILS-based instrumentation and has been previously demonstrated successfully by the inventors for various molecules in the parts per million (ppm) and parts per billion (ppb) concentration range. The following Table II summarizes results achieved for different species, including alcohol as an example for a compound commonly abused as drug:

TABLE II

Absorption Cross Section of Various Molecules Successfully Detected with ILS Instrumentation Including Drugs.

| Molecule | Absorption Cross Section [$cm^2$] |
|---|---|
| $H_2O$ | $8.20 \times 10^{-21}$ |
| $CO_2$ | $5.40 \times 10^{-21}$ |
| $NH_3$ | $22.0 \times 10^{-21}$ |
| $CH_3CH_2OH$ | $4.9 \times 10^{-21}$ |

The comparison given in Table II clearly demonstrates the ability of ILS drug sensors to detect drugs and metabolized drug by-product vapors even when assuming ppb by-product levels inside a vehicle or other enclosed spaces. It can be concluded from this table that detecting drug-impaired vehicle operators with ILS drug sensors is a highly promising approach.

Figure 2:
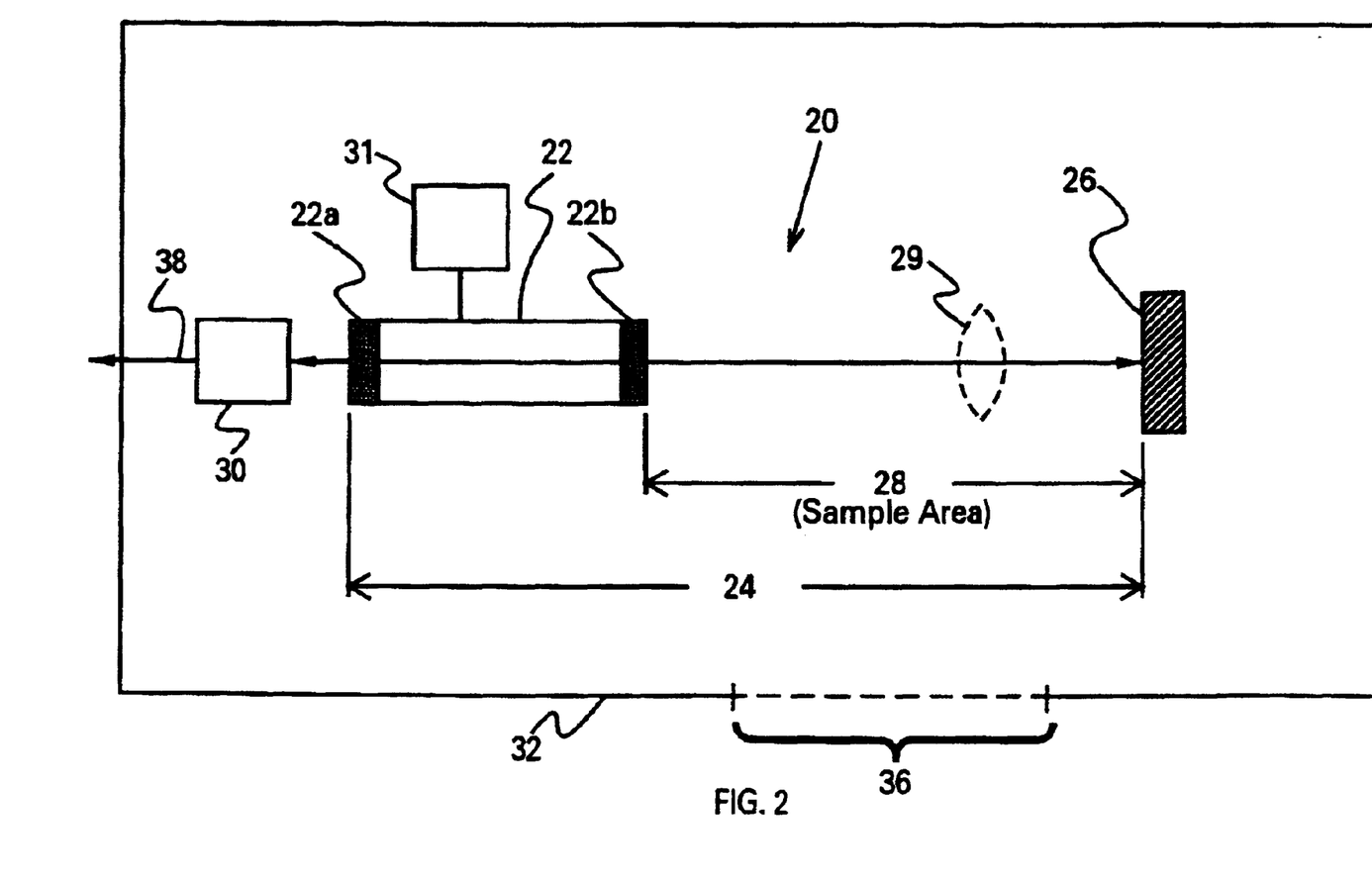
FIG. 2 is a schematic diagram of an on-board drug sensor of the present invention, comprising a diode laser with an external cavity.

An example of an on-board drug sensor in accordance with the present invention and based on a multi-mode diode laser with an external cavity is now described. This approach has been studied in detail experimentally and theoretically for its applicability to ILS measurements and complies with requirements outlined in previous paragraphs. FIG. 2 depicts such a sensor 20, which is configured to detect drug vapors or vaporized metabolized by-products of drugs. Although one specific embodiment is depicted, other configurations of the basic sensor may also be constructed, based on the teachings herein.

In a laser 22 functioning as an intracavity spectroscopic device, a broadband laser resonator 24 is established between a first facet 22a of the laser diode, or gain medium, and a highly reflective end mirror 26. The first facet 22a is provided with a reflectivity coating to effectively utilize the gain of the laser medium to achieve threshold for laser action. A second facet 22b facing the end mirror 26 is preferably anti-reflection coated in order to provide the highest transmission possible and to minimize interference effects. An external cavity region (i.e., sample area) 28 where drug or metabolized by-product molecules are present is established between the end mirror 26 and the anti-reflection coated facet 22b of the laser diode 22. An optical element 29, for example, a lens, may be placed inside the cavity to focus, expand, or collimate light emitted from the internal facet onto the end mirror and the reflected light back into the diode. In this configuration, the external cavity region of the laser resonator itself can be used as the sample cell 28, and the entire assembly 20, with or without a detector 30 (described below) is mounted in a small container or housing 32. The drug or metabolized by-product molecules enter the sample area 28 through an input port 36.

Preferably, the laser 22 is a solid-state laser, for example, a diode laser, for compactness and relatively low power consumption. The laser 22 may be an external cavity diode laser (ECDL) or a superluminescent diode (SLD) laser, for example, and may be driven either electrically or optically (e.g., a second laser or lamp), as shown at 31.

A suitable detector (e.g., a photodiode sensitive to the detection wavelength selected) 30 is mounted next to the first facet 22a of the laser diode 22 and responds to changes in laser intensity, laser wavelength, and/or laser temporal properties altered by changing drug concentrations. The detector 30 provides an output signal 38 that is subsequently employed to provide an indication of threshold drug concentration, as described more fully below. Examples of suitable photodiodes include germanium and (In,Ga)As.

With a similar experimental setup, an absorption coefficient of $10^{-6}$ $cm^{-1}$ has been measured for a rubidium transition in a heat pipe at 780 nm (V. M. Baev et al, *Applied Physics*, vol. B55, pp. 463–477, 1992). Thus, detection drugs or of metabolized by-products of drugs by ECDL/ILS appears to be readily achievable.

In principle, drug detection utilizing on-board ILS sensor systems can be conducted where drugs (e.g., cocaine at 3.45 $\mu$m) or their metabolized by-product molecules are expected to show absorption features (see FIG. 1).

The absorption at 3.45 $\mu$m can possibly be disturbed by methane ($CH_4$) generated by the car engine. No other molecular species present inside a vehicle cabin shows absorption features in the same spectral region. A close examination of literature database absorption reveals distinctive absorption voids in the absorption spectrum of species absorbing around 3.45 $\mu$m, allowing for cocaine detection at this wavelength. (L. S. Rothman, "The Hitran Molecular Database", *J. Quant. Spectrosc. Radiat. Transf.*, Vol. 48, pp. 5/6, 1992).

Since the on-board drug sensor 20 is contained within the sensor housing 32, which completely encloses the laser beam, its use totally obviates any laser radiation damage concerns. It meets emission limit requirements for Class 1 laser systems, which are considered to be safe for humans. In detail, Class 1 laser systems are defined as follows (U.S. Department of Health and Human Services, Public Health Service, Food and Drug Administration, "Regulation for the Administration and Enforcement of the Radiation Control for the Health and Safety Act of 1968", Code of Federal Regulations, Parts 1000 to 1005, 1996):

"Class 1 laser product means any laser product that does not permit access during the operation to levels of laser radiation in excess of the accessible emission limits. Class 1 levels of laser radiation are not considered to be hazardous."

Figure 3:
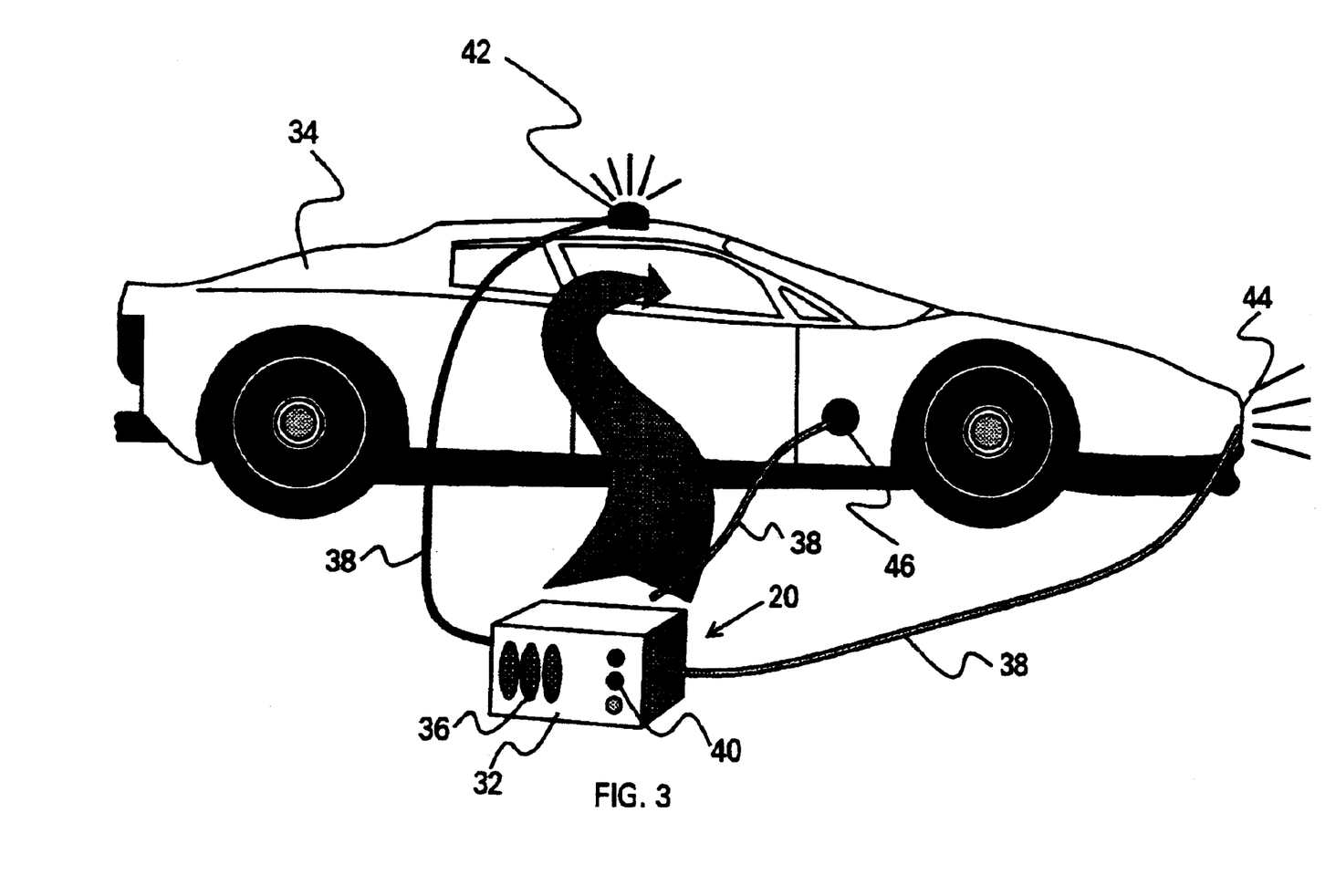
FIG. 3 is a schematic diagram of incorporation of the on-board drug sensor of the present invention in a vehicle, illustrating activation of various internal indicators.

FIG. 3 illustrates several implementations and applications of an on-board ILS drug sensor 20 in a vehicle 34. The housing 32 is provided with a cabin air intake 36, which admits air from the cabin of the vehicle 34 for introduction into the sample area 28 of the sensor 20. The air may enter the sample area 28 by simple diffusion or by use of an active device, such as a fan (not shown) that pushes or pulls air into the sample area.

There are a variety of applications to which a signal 38 from the detector 30 can be directed. These applications include, but are not limited to, (1) internal warning signals, such as a light display 40, perhaps mounted on the housing 32, for alerting the vehicle occupant(s), (2) visible external indicators, such as a flashing light 42 mounted on the vehicle 34 or direct connection from the detector 30 to headlights 44 to cause them to flash, and (3) invisible external indicators (e.g., infrared) warning lights 46 to be detected by the police only or by a remote test station, or by a satellite.

For example, a suitably configured "drug gun" (i.e., configured to detect the output signal 38) aimed at the external indicator 46 could provide the police with a measure of the concentration of drug vapors or metabolized by-product inside the vehicle cabin. Or, test stations, periodically established along a highway, could be configured to sense each vehicle as it passes, "interrogating" the vehicle to determine the drug or by-product concentration therein. Or, in a more sophisticated system, a radio signal could be sent to a satellite and retransmitted to a suitable ground receiving station to provide a measure of the drug or by-product concentration inside the vehicle. In another possible implementation, authorities would be able to use a hand-held drug sensor to interrogate the interior of suspicious vehicles.

Figure 4A:
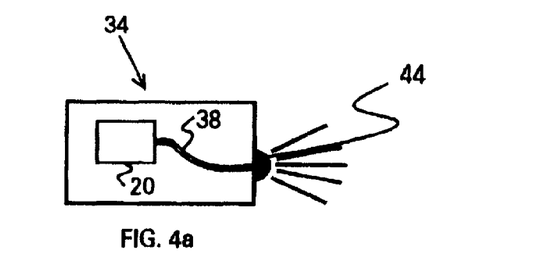
FIGS. 4a–4d are schematic illustrations, depicting four alternate embodiments for emitting a signal representative of drug concentration information to law enforcement personnel by various external indicators, including flashing headlights of the vehicle (FIG. 4a), a "drug gun" (FIG. 4b), a permanent roadside drug detector (FIG. 4c), and a satellite detector for transmission to mobile and/or stationary law enforcement (FIG. 4d).

FIGS. 4a–4d schematically depict various external indicators. FIG. 4a illustrates connection of the on-board ILS sensor 20 to flashing headlights 44 via output signal 38, to enable visual detection of drugs and their by-product concentration by conventional vehicular instrumentation.

Figure 4B:
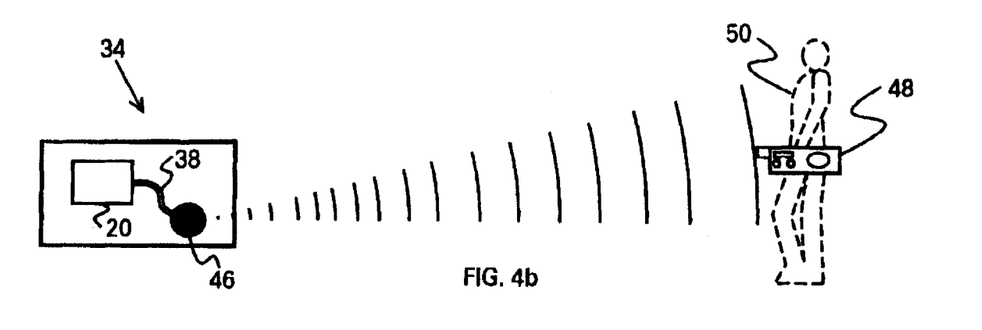

FIG. 4b illustrates connection of the on-board ILS sensor 20 to signal emitter 46 via output signal 38, to enable detection of drugs and their by-product concentration by a "drug gun" 48 operated by law enforcement personnel 50. The drug gun 48 is configured to detect the emitted signal and translate it into drug or metabolized by-product concentration, much like a radar gun is configured to translate motion of a vehicle into speed.

Figure 4C:
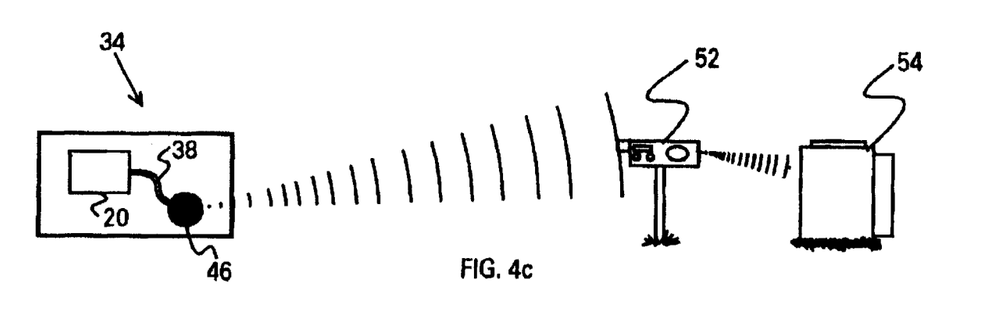

FIG. 4c illustrates connection of the on-board ILS sensor 20 to signal emitter 46 via output signal 38, to enable detection of drug or metabolized by-product concentration by a permanently placed roadside detector 52, which then transmits the information received to mobile and/or stationary law enforcement 54. The roadside detector 52 is configured much like the drug gun 48, and includes additional components for transmission of the information.

Figure 4D:
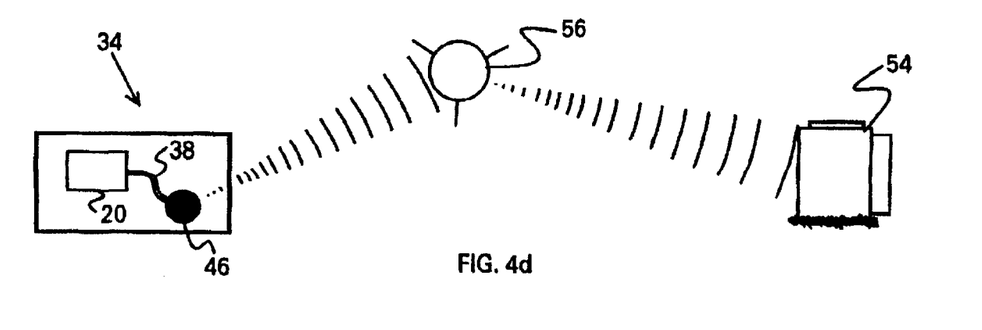

FIG. 4d illustrates connection of the of the on-board ILS sensor 20 to signal emitter 46 via output signal 38, to enable detection of drug or metabolized by-product concentration by a satellite 56, which then transmits the information received to mobile and/or stationary law enforcement 54. The satellite 56 is configured much like the roadside detector 52.

In an alternate embodiment, the ILS sensor 20 may be provided as a hand-carried instrument for detecting drug vapors and/or metabolized by-product vapors in an enclosed space, such as a cargo area, the hold of a ship, etc. In such a case, the instrument would be left in the enclosed area for a period of time to reach a steady state in the detection of such vapors. For example, the "drug-gun" 48 of FIG. 4b could be suitably altered to include the ILS drug sensor 20. Or, the ILS sensor 20, with its associated signal 38 and external indicator, or transmitter, 46, could be placed in such an enclosed area and the signal transmitted to the hand-held receiver 48, as shown in FIG. 4b.

INDUSTRIAL APPLICABILITY

The on-board drug sensor of the present invention is expected to find use in vehicles to provide drivers and law enforcement officials with an indication of any drugs or metabolized by-product vapors inside the vehicle cabin resulting from exhalation by drug-taking drivers or the presence of drugs inside the vehicle.

Thus, there has been disclosed an on-board drug sensor for detection of drugs and metabolized by-product vapors in vehicular cabins. It will be readily appreciated by those skilled in this art that various changes and modifications of an obvious nature may be made, and all such changes and modifications are considered to fall within the scope of the invention, as defined by the appended claims.

What is claimed is:

1. An ILS sensor for detecting the presence of drug vapors, other than ethyl alcohol vapors, or metabolized by-product vapors in an enclosed space, said sensor, comprising:

(a) a laser comprising a gain medium having two opposed facets within a laser resonator and functioning as an intracavity spectroscopic device having a first end and a second end, said first end operatively associated with a partially reflecting surface;

(b) a reflective or dispersive optical element operatively associated with said second end to define a broadband wavelength laser resonator between said optical element and said first end and to thereby define an external cavity region between at least one facet of said gain medium and either said first end or said second end or both ends;

(c) said external cavity region being exposed to air in said enclosed space to enable any drug vapors or metabolized by-product molecules to enter thereinto;

(d) a detector spaced from said first end and providing an output detector signal;

(e) electronic means for measuring and analyzing said detector signal;

(f) a housing for containing at least said laser, said partially reflecting surface, and said optical element, said housing being configured to prevent escape of stray radiation into said enclosed space and to permit air from said enclosed space to continuously circulate through said external cavity region for analysis; and (g) means for driving said laser.

2. The ILS sensor of claim 1 wherein said gain medium has an anti-reflective coating to maximize transmission and minimize interference effects.

3. The ILS sensor of claim 1 wherein said first end has a reflectivity to effectively utilize the gain of the laser medium to achieve threshold for laser action.

4. The ILS sensor of claim 1 wherein said reflective or dispersive optical element comprises a mirror or a diffraction grating, respectively.

5. The ILS sensor of claim 1 wherein said detector comprises a photodiode sensitive to a selected wavelength related to an absorption frequency of said drug vapors or metabolized by-product.

6. The ILS sensor of claim 5 wherein said wavelength is within a range of about 1 to 4 μm.

7. The ILS sensor of claim 6 wherein said wavelength is selected to be about 3.45 μm for cocaine.

8. The ILS sensor of claim 1 wherein said detector is operatively associated with an internal indicator.

9. The ILS sensor of claim 1 wherein said detector is operatively associated with an external indicator.

10. The ILS sensor of claim 9 wherein said external indicator is a light mounted external to said enclosed space.

11. The ILS sensor of claim 9 wherein said external indicator is accessible by a portable sensor or a remote test station or transmits a signal to a satellite.

12. The ILS sensor of claim 1, wherein said detector is capable of detecting said drug vapors or metabolized by-product vapors in a concentration of at least 1 part per billion.

13. The ILS sensor of claim 1 wherein said laser is selected from the group consisting of external cavity diode lasers and superluminescent diode lasers.

14. The ILS sensor of claim 1, wherein said detector comprises a photodiode.

15. The ILS sensor of claim 1, wherein said enclosed space is a cabin of a vehicle and said drug vapors or metabolized by-product vapors result from the presence of drugs or drug use by a driver.

16. A method for measuring concentration of vapors, other than ethyl alcohol vapors, resulting from drug presence or metabolization of such drugs and representative of air in an enclosed space employing an ILS sensor comprising (a) a laser comprising a gain medium having two opposed facets within a laser resonator and functioning as an intracavity spectroscopic device having a first end and a second end, said first end operatively associated with a partially reflecting surface;

(b) a reflective or dispersive optical element operatively associated with said second end to define a broadband wavelength laser resonator between said optical element and said first end and to thereby define an external cavity region between at least one facet of said gain medium and either said first end or said second end or both ends;

(c) said external cavity region being exposed to air in said enclosed space to enable any drug vapors or metabolized by-product vapors to enter thereinto;

(d) a detector spaced from said first end;

(e) electronic means for measuring and analyzing said detector signal;

(f) a housing for containing at least said laser, said partially reflecting surface, and said optical element, said housing being configured to prevent escape of stray radiation into said enclosed space and to permit air from said enclosed space to continuously circulate through said external cavity region for analysis; and (g) means for driving said laser, said method comprising:

(1) sensing any said drug vapors or said metabolized by-product vapors representative of air in said enclosed space by said ILS sensor; and (2) providing a signal indicative of presence of any said drug vapors or said metabolized by-product vapors.

17. The method of claim 16 wherein said signal is internal to said enclosed space and provides a warning to an occupant within said enclosed space.

18. The method of claim 16 wherein said signal is external to said enclosed space.

19. The method of claim 18 wherein said signal activates an external indicator comprising a light external to said enclosed space.

20. The method of claim 18 wherein said signal activates an external indicator that is accessible by a portable sensor or a remote test station or transmits a signal to a satellite.

21. The method of claim 16 wherein said detector is capable of detecting drug vapors or metabolized by-product vapors in a concentration of at least 1 part per billion.

22. The method of claim 16 wherein said enclosed space is a cabin of a vehicle and said drug vapors or metabolized by-product vapors result from the presence of drugs or drug use by a driver.

* * * * *